United States Patent
Friedland et al.

(12) 
(10) Patent No.: US 6,303,153 B1
(45) Date of Patent: Oct. 16, 2001

(54) PREPARATION OF A THERAPEUTIC COMPOSITION

(75) Inventors: Bernard Friedland, Sarasota, FL (US); Shalom Z. Hirschman, Riverdale, NY (US)

(73) Assignee: Advanced Viral Research Corp., Hallandale, FL (US)

( * ) Notice: Subject to any disclaimer, the term of this patent is extended or adjusted under 35 U.S.C. 154(b) by 0 days.

(21) Appl. No.: 09/344,095

(22) Filed: Jun. 25, 1999

Related U.S. Application Data

(63) Continuation-in-part of application No. 08/735,236, filed on Oct. 22, 1996, now abandoned.

(51) Int. Cl.$^7$ .................................................. A61K 38/01

(52) U.S. Cl. ..................... 424/529; 424/535; 424/548; 424/195.1; 514/2; 514/21; 514/44

(58) Field of Search .................................. 424/535, 529, 424/195.1, 548; 514/2, 21, 44

(56) References Cited

U.S. PATENT DOCUMENTS

| | | | | |
|---|---|---|---|---|
| 5,807,839 | * | 9/1998 | Hirschman | 514/44 |
| 5,807,840 | * | 9/1998 | Hirschman | 514/44 |
| 5,849,196 | * | 12/1998 | Kochel | 210/651 |
| 5,902,786 | * | 5/1999 | Bregman | 514/2 |

OTHER PUBLICATIONS

Cooke, Stanford B., Upper Respiratory Viral Manifestations, Clinical Symposium on Viral Diseases Demonstrating the Anti–viral Biotic Properties of the Drug Reticulose (Symposium), Sep., 1960, Miami Beach, Florida, pp. 25–32.

Kosaka, K and Shimada, Y., Infectious Hepatitis, Symposium, pp. 61–74, 1960.

Kuckku, Morris E., Herpetic Diseases, Symposium, pp. 7–13, 1960.

Medoff, Lawrence R., Infectious Mononucleosis, Symposium, pp. 33–37, 1960.

Plucinski, Stanisloff J., Suspected Viral Varieties, Symposium, pp. 53–59, 1960.

Reynolds, Margaret R., Generalized Vaccinia, Symposium, pp. 5–6, 1960.

Schaeffer, Oden A., Influenza, Symposium, pp. 15–21, 1960.

Seydel, Frank, Epidemic, Asian Influenza, Symposium, pp. 23–24, 1960.

Anderson, Robert H., Encephalitis, Symposium, pp. 39–52, 1960.

Anderson, Robert H. and Thompson, Ralph M., Treatment of Viral Syndrome with a Lipoprotein–Nucleic Acid Compound (Reticulose), A Report of Five Cases, Virginia Medical Monthly, 84: 347–353, 1957.

Reynolds, Margaret R., Generalized Vaccinia Successfully Treated With Lipoprotein–Nucleic Acid Complex (Reticulose), Archives of Pediatrics, 77:421–422, 1960.

Kozima, Fumio, Osawa, Mitsuo and Oyama, Mitsuko, Animal Tests on Reticulose ("Key"), Kensan Report No. Sho 43–22, Sep. 4, 1968.

(List continued on next page.)

Primary Examiner—Jean C. Witz
(74) Attorney, Agent, or Firm—Cohen, Pontani, Lieberman & Pavane

(57) ABSTRACT

Product R, a novel therapeutic composition for treating viral infections and stimulating the immune system, comprises nucleotides and peptides that have molecular weights not more than 14 KDa and substantially not more than 8 KDa. The composition has a light absorption spectrum with typical absorption ratios of 1.998 at 260 nm/280 nm and 1.359 at 260 nm/230 nm.

11 Claims, 8 Drawing Sheets

(2 of 8 Drawing Sheet(s) Filed in Color)

OTHER PUBLICATIONS

Wegryn, Stanley P., Marks, Robert A. and Baugh, John R., Herpes Gestationis, A Report of 2 Cases, American Journal of Obstetrics and Gynecology, 79:812–814, 1960.

Catterall, R.A., Lumpur, Kuala, A New Treatment of Herpes Zoster, Vaccinia And Chicken Pox, J. Roy. Coll. Gen. Practit., 1970, 19, 182.

Chinnici, Angelo A., Reticulose in Treatment Aids patients, Personal Communication to William Bregman, Jul. 6, 1992.

Cott, Rafael A., Summary of 11 Cases of Viral Infections Treated with Reticulose, Private Communication with Advance Viral Research Corp., 1992?.

Cohen, Matthew, The Efficacy of a Peptide–Nucleic Acid Solution (Reticulose) for the Treatment of Hepatitis A and Hepatitis B—a Preliminary Controlled Human Clinical Trial, J. Roy. Soc. Health, Dec., 1992, 266–270.

Mundschenk, David D., In Vitro Antiviral Activity of Reticulose vs Influenaz A, Personal Communication with William Bregman, May 1, 1990.

Resnick, Lionel, Anti–HIV in Vitro Activitiy of Two Samples of Peptide–nucleic Acid Solution, Personal Communication with Dr. Bernard Friedland, Dec. 22, 1989.

Friedland, Bernard, In Vitro Antiviral Activity of a Peptide–Nucleic Acid Solution Against the Human Immunodeficiency Virus and Influenza A Virus, J. Roy. Soc. Health, Oct. 1991, 170–171.

Brazier, Anne D., Method for in Vitro Antiviral Evaluation Human Immunodeficiency Virus (HIV), Personal Communication with Dr. Bernard Friedland, Oct. 4, 1989.

Behbehani, Abbas M., Haberman Sol and Race, George J, The Effect of Reticulose on Viral Infections of Experimental Animals, Southern Medical Journal, Feb., 1962, 185–188.

Treatment of Viral Diseases with A Lipo–protein Nucleic Acid Complex (Reticulose)—A Clinical Study, Scientific Exhibit: Virginia State Medical Society Meeting, Washington, D.C., Nov., 1957.

Kempe, Henry C., Fulginiti, Vincent A., and Vincent, Leone St., Failure to Demonstrate Antiviral Activity of Reticulose, Diseases of Children, vol. 103, No. 5, 655–657, 1962.

Sanders, Murray, Controlled Animal Studies with Reticulose Illustrating the Interference of Lipoprotein–Nucleic Acid Complex in the Experimental Animal Infected with Human Pathogenic Viral Entities, Southern Medical Association Scientific Exhibit, Dallas, Texas, Nov., 1961.

* cited by examiner

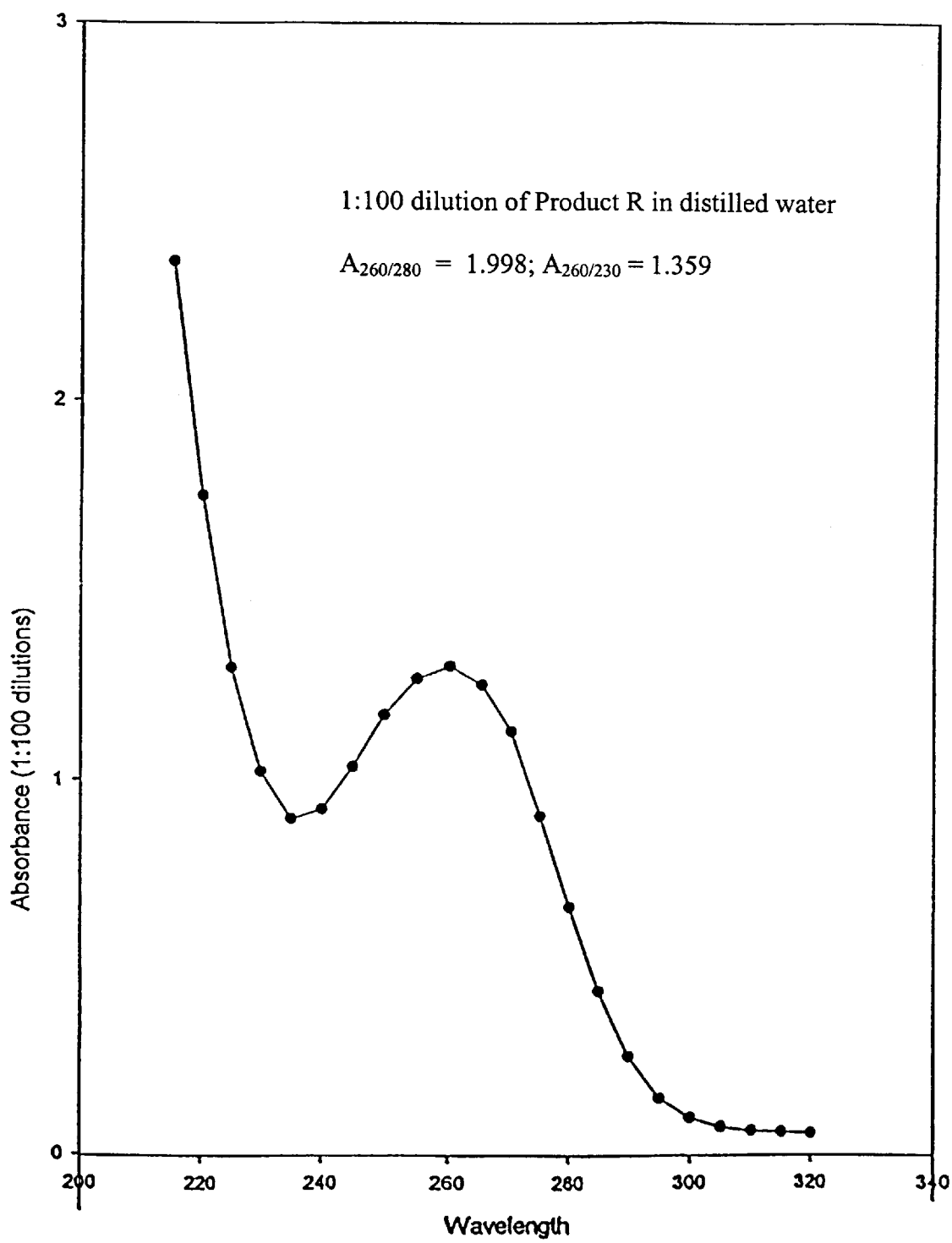
Figure 1. Ultraviolet Spectrum of Product R

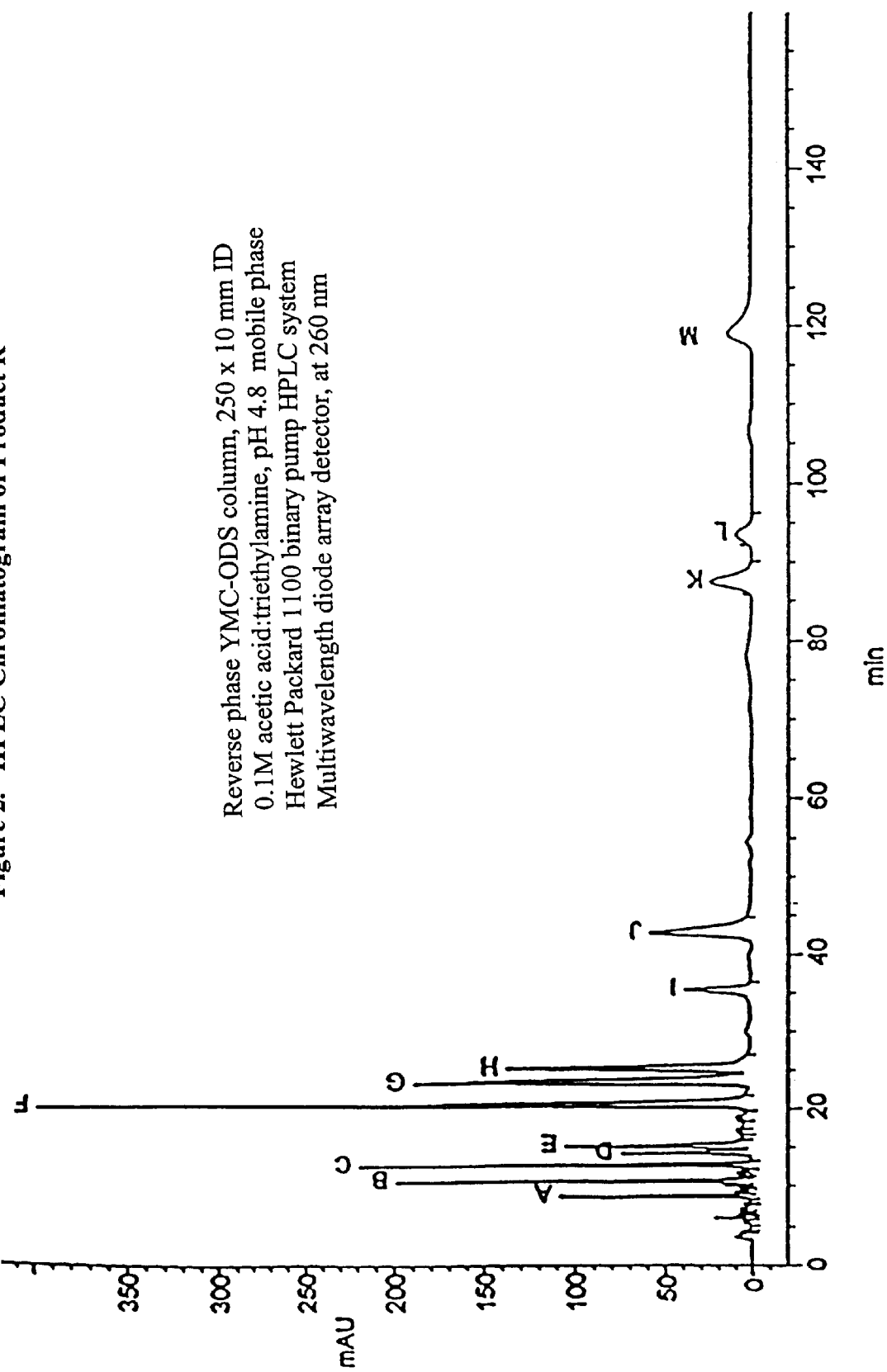
Figure 2. HPLC Chromatogram of Product R

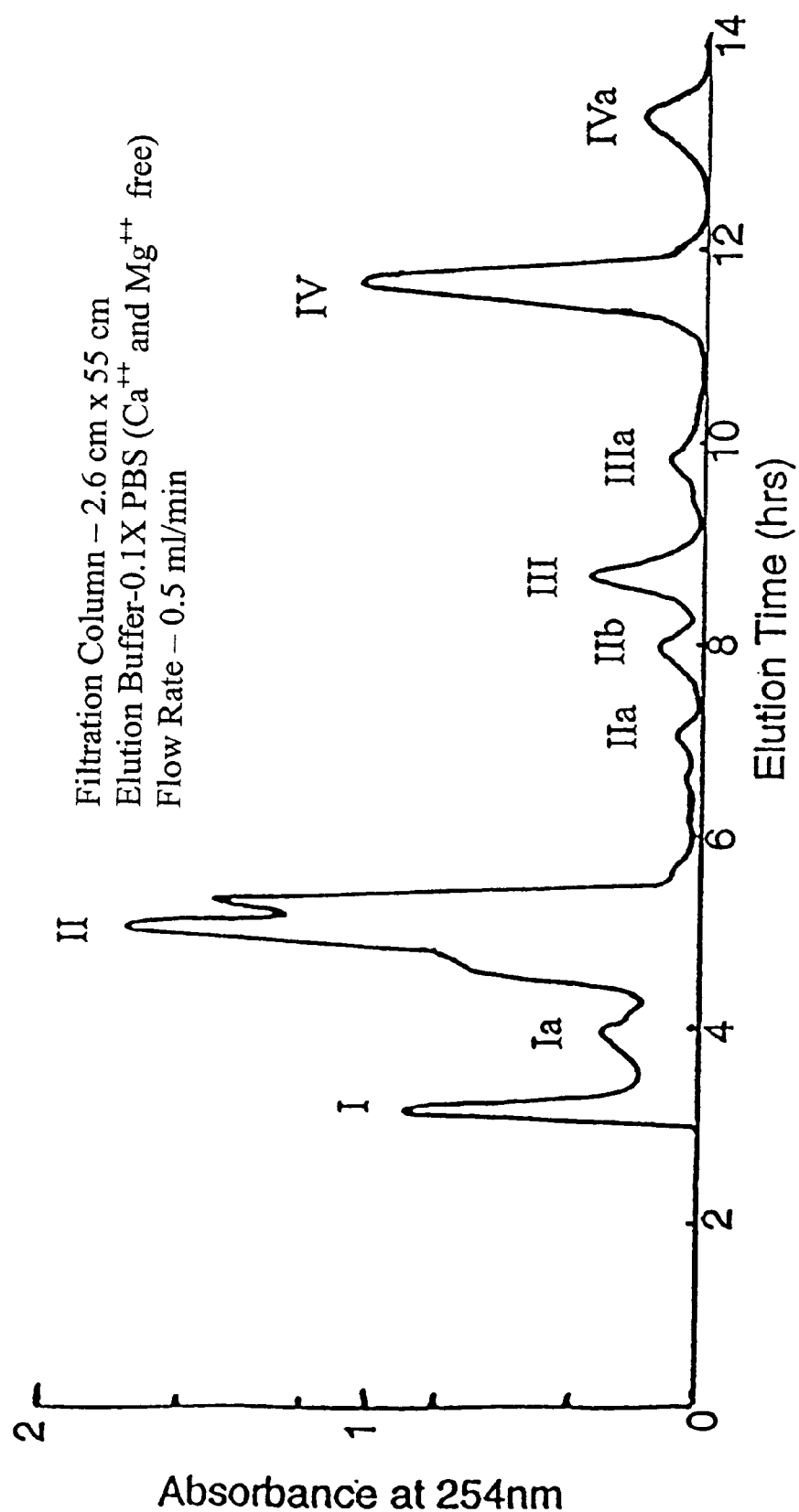
Figure 3. Fractionation of Product R by BioGel P-2 Column

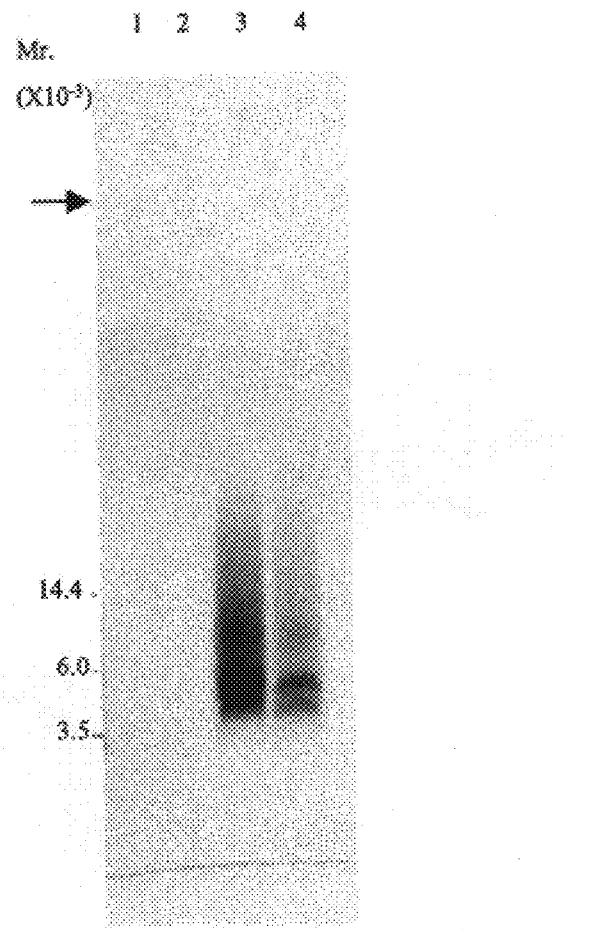

Figure 4.  SDS-Polyacrylamide Gel Electrophoresis of Product R and Fractions

Product R and Peak I fractions show two strong silver stained bands. Later fractions show no band.

Fractions were ten-fold concentrated; 2 ul of Product R and 1 ul of concentrated fractions were used.

Lane 1: Concentrated Peak II; Lane 2: Concentrated Peak Ia; Lane 3: Concentrated Peak I; Lane 4: Product R. Arrow indicates the top of the lane.

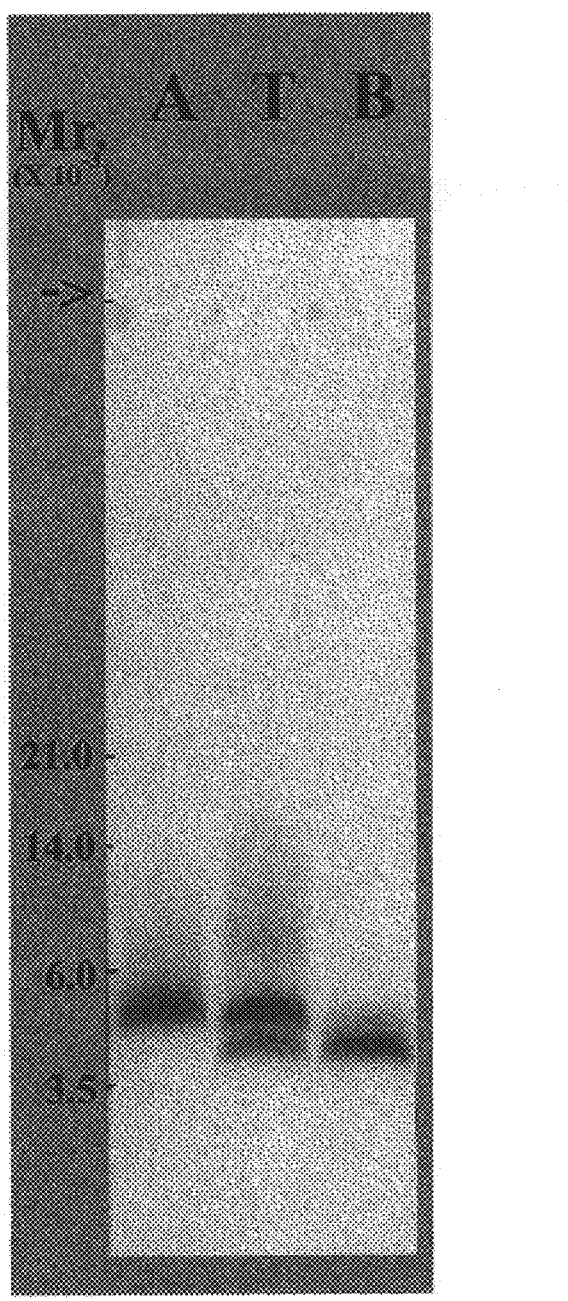
A-Fraction A
T-Total Product R
B-Fraction B
Figure 5. SDS-PAGE Profile of Product R Peptides

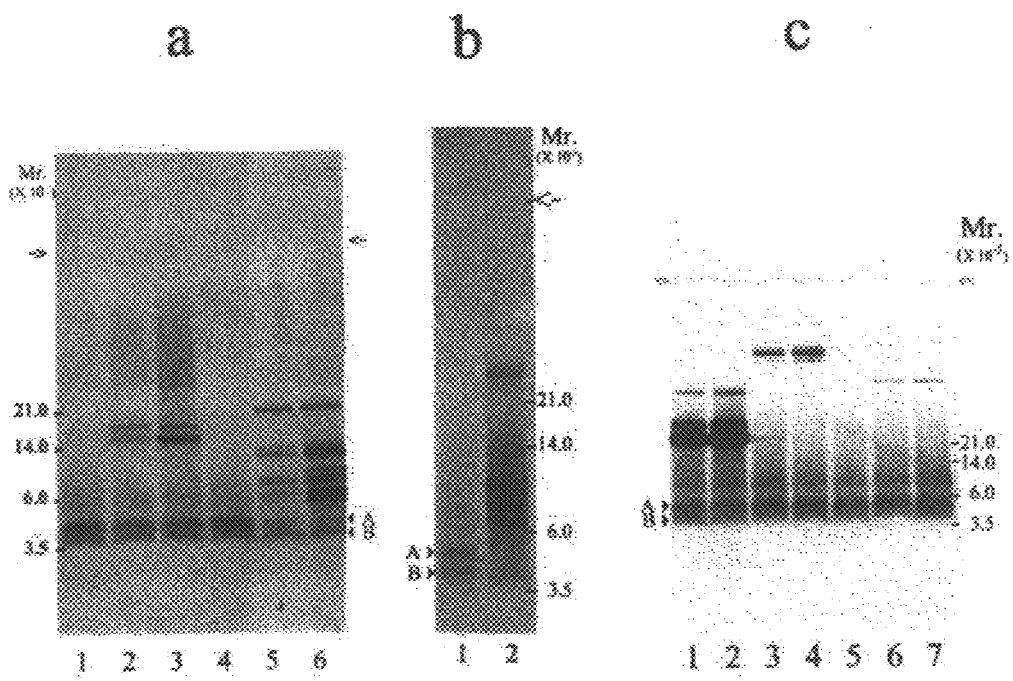

Figure 6. Sensitivity of Product R to Catabolic Enzymes

→, starting point of gel

Panel a, lane 1, Product R in Trypsin reaction buffer;
lane 2, Product R treated with Trypsin (0.05 mg/ml);
lane 3, Product R treated with Trypsin (0.025mg/ml);
lane 4, Product R in Chymotrypsin reaction buffer;
lane 5, Product R treated with Chymotrypsin (0.05mg/ml); and
lane 6, Product R treated with Chymotrypsin (0.025mg/ml).

Panel b, lane 1, Product R in Proteinase K reaction buffer; and
lane 2, Product R treated with Proteinase K (0.8mg/ml).

Panel c, lane 1, Product R treated with Ribonuclease A (0.5mg/ml);
lane 2, Product R treated with Ribonuclease A (1.0mg/ml);
lane 3, Product R treated with Alkaline Phosphatase (100units/ml);
lane 4, Product R treated with Alkaline Phosphatase (200units/ml);
lane 5, Untreated Product R;
lane 6, Product R treated with N-glycosidase F (20 units/ml); and
lane 7, Product R treated with N-glycosidase F (50 units/ml).

Note: All bands other than the 5.2 KDa and the 4.3 KDa bands represent either the enzymes themselves or the fragments of those enzymes.

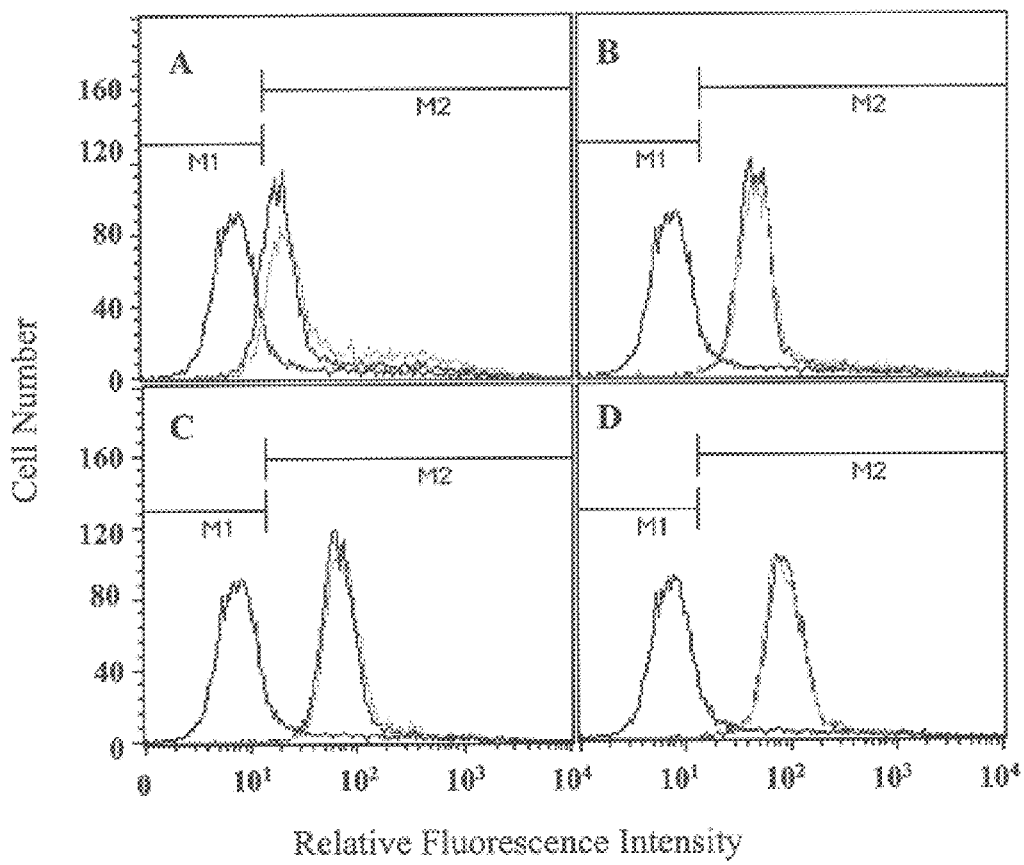

Figure 7. Effects of Product R upon phagocytosis of Dextran-FITC by U937 cells after 24 hr drug treatment. U937 cells were cultured with 5% Product R, or PBS as control, for 24 hr. Cells were harvested, washed and resuspended in binding buffer (RPMI 1640, 10% FCS, 1mM sodium pyruvate, 25 mM Hepes, and 1mg/ml glucose) containing 5 mg/ml Dextran-FITC. These cells were warmed to 37°C for A) 5 min, B) 15 min, C) 30 min , and D) 45 min to allow for phagocytosis. As a control cells were kept at 0°C for the entire incubation period. At the end of each incubation, cells were washed in binding buffer, fixed in 1% formaldehyde/PBS, and analyzed by flow cytometry using a FACSCalibur instrument (Becton Dickinson). The results were analyzed using CellQuest software supplied by the manufacturer. Graphs illustrated represent the relative fluorescence measured as a function of cell number. The following conditions are illustrated: green line = +PBS (control), purple line = +Product R, and black line = 0 min control.

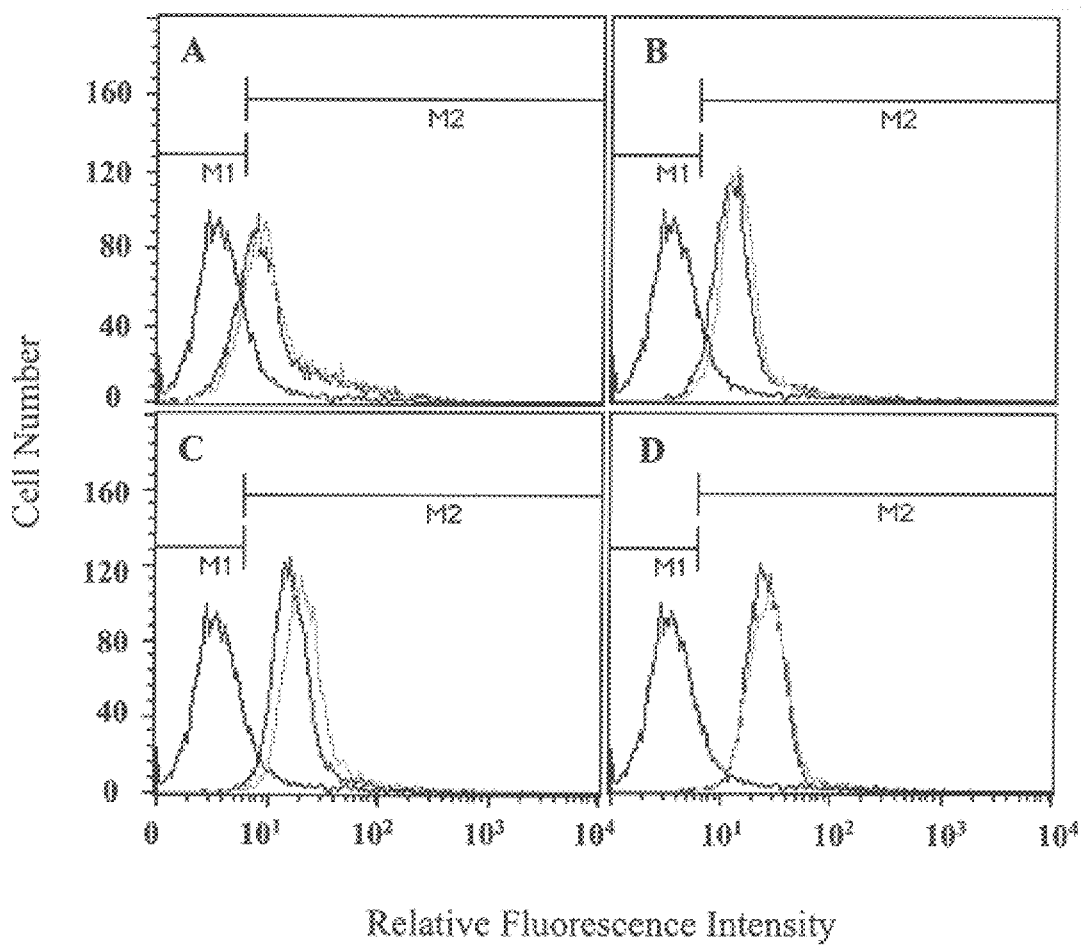

Figure 8. Effects of Product R upon phagocytosis of Dextran-Bodipy FL after an 8 day drug treatment. U937 cells were cultured with 5% Product R, or PBS, for 8 days. To measure phagocytosis, cells were treated similar to the description in Fig. 7, except cells were incubated with 5 mg/ml Dextran-BoDipy FL. These cells were warmed to 37°C for A) 5 min, B) 15 min, C) 25 min, and D) 40 min to allow for phagocytosis. Graphs illustrated represent the relative fluorescence measured as a function of cell number. The following conditions are illustrated: green line = +PBS (control), purple line = +Product R, and black line = 0 min control.

PREPARATION OF A THERAPEUTIC COMPOSITION

RELATED APPLICATIONS

This is a continuation-in-part application of the applicant's pending application Ser. No. 08/735,236, filed on Oct. 22, 1996, now abandoned. This application incorporates contents of the application Ser. No. 08/735,236 by reference in their entirety.

BACKGROUND OF THE INVENTION

1. Field of the Invention

The present invention relates to an improved method of making a therapeutic composition, Product R[1], as hereinafter defined, which contains peptides and nucleotides. The components of Product R have molecular weights not more than 14 kilodaltons (KDa).

Product R was used as synonyms of RETICULOSE in some literature. For the purpose of the present application, Product R and RETICULOSE represent two distinct products.

2. Description of the Related Art

The concept of an antiviral agent composed of peptones, peptides, proteins and nucleic acid was originated in 1934. After some years of experimentation, such an antiviral agent was modified by using bovine serum albumin in combination with peptone, and ribonucleic acid to produce an antiviral biotic agent which is nontoxic, free from anaphylactogenic properties and is miscible with tissue fluids and blood sera. The agent used to be described as a "lipopeptide-nucleic acid compound"[2] and registered under trademark RETICULOSE® by Chemico Laboratories, Inc. Physician Desk Reference, p 651, 1960. RETICULOSE® was reported as an antiviral agent for treating a variety of human viral infections, such as influenza, herpes, hepatitis A and B. It was then assumed that RETICULOSE® acts as an antiviral agent at least by increasing leukogenesis, synthesis of antibodies and enhancing phagocytosis. RETICULOSE® was last sold in the United States in 1964.

The method of making RETICULOSE® had been kept as a trade secret by the manufacture until the issuance of U.S. Pat. No. 5,849,196, which discloses the method of making RETICULOSE®.

As disclosed in U.S. Pat. No. 5,849,196, the starting materials for making RETICULOSE® consist of, by weight, 40–50% of casein, 1–10% of blood albumin, 15–40% of beef peptone, 10–25% of RNA and 5–25% of sodium hydroxide. These starting materials are suspended in water which yields a ratio of proteins (casein, peptone and blood albumin) to water equals to about 4.3 to about 100 by weight. After an autoclaving treatment of the mixture of the starting materials, the resulting solution is filtered and pH is adjusted to approximately 8.5 and then to 7.8, after which the neutralized solution is filtered again. The pH is further adjusted to approximately 7.5 after the solution is diluted. Such process yields a mixture of peptides and nucleic acids having molecular weights in a range of approximately 1 to 25 KDa.

As taught by U.S. Pat. No. 5,849,196, the components over 15 KDa of the conventional composition of RETICULOSE® are more effective in treating viral diseases such as HIV, influenza virus, herpes simplex virus, etc. while the components in a range of approximately 1 to 15 KDa function as phagocytosis inhibitors.

However, the conventional methods suffers from several disadvantages: 1) the method does not ensure that each preparation produces the finished components having the same ratio, thereby the product is not reproducible; 2) the conventional method produces a wide range of the finished components, which makes the quality control of the preparation extremely difficult, if possible, because too many parameters need to be determined; 3) the presence of the higher molecular weight components, such as 25 KDa component, essentially peptides, increases the risk of hypersensitivity or immune reaction and renders the product less stable.

Therefore, it is desirable to have a product devoid of the deficiencies of conventional RETICULOSE® while maintaining its therapeutic properties.

SUMMARY OF THE INVENTION

Accordingly, an object of the present invention is directed to a novel therapeutic composition, Product R. Unlike RETICULOSE®, Product R is reproducible, highly stable and non-antigenic. Similar to RETICULOSE®, Product R is a wide range antiviral agent for treating viral infections such as infections of human immnunodeficiency virus (HIV), herpes simplex virus, adenovirus and papilloma virus. Surprisingly, Product R has been proven to be effective in stimulating the production of chemokines including interferon-gamma, interleukin-6 and interleukin-1 (J. Investig Med 1996; 44:347–351), the production of red blood cells (U.S. Pat. No. 5,807,839), treating basal cell carcinoma (U.S. Pat. No. 5,902,786) and treating canine distemper viral infections (U.S. Pat. No. 5,807,840).

Another object of the present invention is directed to an improved method for making the novel therapeutic composition Product R. Product R according to the present improved method comprises novel components that generate a novel UV absorption spectrum and a novel molecular weight profile. Particularly, Product R comprises molecules having molecular weights not more than 14 KDa.

A further object of the present invention is to define the components of Product R based on chemical and physical methods.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The file of this patent contains at least one drawing executed in color. Copies of this patent with color drawings will be provided by the Patent and Trademark Office upon request and payment of the necessary fee.

In the drawings:

FIG. 1 shows a representative ultraviolet absorption profile of Product R;

FIG. 2 shows a representative chromatogram of Product R obtained form a reverse phase HPLC analysis;

FIG. 3 shows a BioGel P-2 fractionation profile of Product R;

FIG. 4 shows the components of fraction I of the BioGel P-2 fractionation profile resolved on a 16% of SDS-Polyacrylamide gel electrophoresis (SDS-PAGE);

FIG. 5 shows the relative mass (Mr.) of the two major peptide components of Product R resolved on a 16% SDS-PAGE;

FIG. 6 is a 16% SDS-PAGE, showing the effects of a variety of catabolic enzymes on Product R;

FIG. 7 is a flow cytometric histograms, showing the effect of Product R on phagocytosis of Dextran-FITC; and FIG. 8 is a flow cytometric histograms, showing the effect of Product R on phagocytosis of Dextran-BoDipyFL.

DETAILED DESCRIPTION OF THE PRESENTLY PREFERRED EMBODIMENTS

Preparation of Product R

Generally, Product R is prepared according to the following manner.

First, the starting materials casein, beef peptone, RNA, BSA, and sodium hydroxide are suspended in proportions of, by weight, 35–50% (casein), 15–40% (beef peptone), 10–25% (RNA), 1–10% (BSA) and 5–25% (sodium hydroxide) in an appropriate volume of distilled water. All starting materials are generally available or otherwise can be readily prepared by a person of ordinary skill in the art. While any RNA is suitable for the intended purpose of the present invention, plant RNA is preferred and yeast RNA is the most preferred. The ratio of total proteins versus the volume of distilled water is generally about 1.5–2.5 to about 100 by weight, preferably about 2.2 to about 100 by weight. This means that every 1.5–2.5 grams of the total proteins are suspended in about 100 milliliters of distilled water.

All the starting materials are either generally commercially available or can be readily prepared by a person of ordinary skill in the art.

The suspension as prepared above is then autoclaved at a pressure of approximately 5–15 lbs., preferably 8–10 lbs. under an elevated temperature in a range, for example about 150°–300° F. preferably about 200°–230° F. over a period of approximately 2–10 hours, preferably more than 3 hours. As known to a person of ordinary skill in the art, under such conditions RNA may be completely hydrolyzed into nucleotides. After autoclaving, the solution is cooled down to room temperature, and then allowed to stay at a temperature of 3° to 8° C. for at least 12 hours to precipitate insoluble elements. Alternatively, the cooled solution may be centrifuged at a temperature below 8° C. to remove the precipitates.

The resulting solution is then filtered through a 2 micron and a 0.45 micron filters under an inert gas such as nitrogen or argon at a pressure of about 1–6 psi. In a similar manner the solution is filtered again through a pyrogen retention filter, preferably 0.2 micron.

After the above filtration, the solution may be cooled at 3 to 8° C. again for at least about 12 hours and filtered again in the same way as described above.

The resulting filtrate is then assayed for total nitrogen content using methods known to a person of ordinary skill in the art such as Kjeldahl method, J. G. C. D. Kjeldahl, Z. Anal. Chem., Vol. 22, p366 (1883), and its improvements. Based on the assay, the filtrate is then diluted with chilled distilled water to an appropriate volume having a preferred total nitrogen content ranging from 165 to 210 mg/ml.

The pH of the diluted solution is then adjusted with HCl to a physiologically acceptable pH, preferably to about 7.3 to 7.6, after which the diluted solution is filtered again through a 0.2 micron filter under an inert gas as described above.

Product R so produced contains essentially nucleotides, nucleosides and free nucleic acid bases of low molecular weights from a complete hydrolysis of RNA and small peptides from partial hydrolysis of the proteins. It is possible that the base hydrolysis of the proteins also produces free amino acids.

It is understood that the use of filtration technique is essentially to remove bacteria or other particles having similar size to or larger size than bacteria. Thus, any filter regardless its manufacturer or material from which it is made is suitable for the intended purpose. All filters used in the present process are widely available to a person of ordinary skill in the art.

The final filtrate is then filled and sealed into appropriate vials, such as 2 ml or 10 ml glass vials under an inert gas. The filled vials are autoclaved for final sterilization, after which they are ready for use.

In use, Product R is administered parenterally or topically to a patient in need as described in U.S. Pat. Nos. 5,807,839, 5,807,840 and 5,902,786, the contents of which are herein incorporated by reference in their entirety.

Characterization of Product R

The ultraviolet absorption spectrum:

FIG. 1 is a representative ultraviolet absorption spectrum of Product R measured in 1 cm path length quartz microcuvette (100 μl capacity) using a Shimadzu Model UV-1201 UV-VIS Spectrophotometer. Product R was diluted with distilled water by 100 fold. The spectrum is recorded between 220–320 nm and shows a maximum absorption at 260 nm and a trough at 235 nm. The ratio of the absorbance (A) at 260 nm over absorbance at 280 nm is 1.998 (±10%), and A at 260 nm over A at 230 nm is 1.359 (±10%).

The HPLC profile:

FIG. 2 is a representative chromatogram of Product R obtained from a reverse phase HPLC analysis using a Hewlett Packard 1100 HPLC system (Hewlett Packard Co.) that includes a binary pump (Model G1312A), a diode array detector (Model G1315A), a column thermostat (Model G 1316A), a thermostatted autosampler (Model G1329A), a sample thermostat and a vacuum degasser (Model G 1322A); and a stainless steel YMC-pack ODS-AQ S-5 uM column (YMC, Inc. 3223 Burnt Mill Dr., Wilmington, N.C. 28403) that has a size of 250×10 mm ID and pore size 120 A. The mobile phase consisting of a 0.1 M acetic acid: trietheylamine is prepared as follows: 6.0 ml of glacial acetic acid are dissolved in 1000 ml of HPLC grade water. The stirred solution of acetic acid is titrated with triethylamine to pH 4.8. The solution is allowed to equilibrate overnight at room temperature and then filtered through a 0.45 μM pore size and 52 mm diameter filter. The pH of the solution is readjusted to pH 4.8 if necessary with the addition of triethylamine prior to use. The mobile phase is degassed by the vacuum degasser built into the HPLC flow system. 8 μl of Product R sample are injected, by means of an autosampler, into the column having a temperature set at 30° C. for each injection. The sample is then isocratically eluted from the column with 0.1 M acetic acid: triethylamine mobile phase (pH 4.8) at a rate of 1 ml per minute under a pump pressure of 92–102 bar. The chromatograms (UV absorbences at 260 nm) are run at 160 minutes per sample and the data are collected by the diode array detector and then analyzed using Hewlett-Packard HPLC ChemStation software. Graphical plots are generated and statistical analysis is conducted using the SigmaPlot program. The reverse phase HPLC under such conditions results in 13 characteristic HPLC peaks: A, B, C, D, E, F, G, H, I, J, K, L and M, each of which has a characteristic UV absorption profile (data not shown).

The BioGel P-2 gel filtration profile:

FIG. 3 shows a fractionation profile of Product R on a BioGel P-2 (Bio-Rad Laboratories Inc.) column having a size of 2.6 cm×55 cm packed size. After loading of Product R to the column, the column is eluted with a 0.1X PBS, preferably DULBECCO's PBS, free of calcium ion ($Ca^{++}$) and magnesium ion ($Mg^{++}$), at a flow rate of 0.5 milliliters per minute. 1X PBS contains 1.47 mM $KH_2PO_4$, 2.67 mM KCl, 138 mM NaCl and 8.1 mM $Na_2HPO_4$ $7H_2O$. The eluent passes through a "Uvcord SII" monitor, which is attached to a REC 101 chart recorder and fitted with a 254 nm filter, and is collected at 12 minutes per fraction in a "Frac 200" fraction collector. The gel filtration chromatography under such conditions results in 9 fractions: I, Ia, II, IIa, IIb, III, IIIa, IV and IVa. Each individual peak is compared with known nucleotides, nucleosides and free nucleic acid bases eluted at the same or very close to the volumes of respective fractions as shown in TABLE I. Known compounds having comparable values are shown in Remarks column.

TABLE I

| Peak | λmax | λmin | $A_{260}/A_{280}$ | $A_{260}/A_{230}$ | Remarks |
|---|---|---|---|---|---|
| Peak I | ~275 nm | ~255 nm | 0.976 | 0.300 | Mostly peptides and peptide conjugates |
| Peak Ia | ~260 nm | ~240 nm | 1.636 | 0.943 | Nucleoprotein and/peptide nucleic acid |
| Peak Is | ~270 nm | ~245 nm | 1.258 | 0.939 | Major component is CMP |
| Peak IIα | ~260 nm | ~230 nm | 2.893 | 3.12 | Major components are AMP, UMP |
| Peak IIβ | ~250 nm | ~225 nm | 1.509 | 1.988 | Major component is GMP |
| Peak IIa | ~250 nm | ~230 nm | 1.257 | 1.176 | Mixed components |
| Peak IIb | ~270 nm | ~250 nm | 1.142 | 0.941 | Major component is Cytidine |
| Peak III | ~260 nm | ~230 nm | 2.695 | 3.664 | Major component is Uridine |
| Peak IIIa | ~260 nm | ~225 nm | 5.15 | 4.24 | Major components are Uracil, Adenosine |
| Peak IV | ~260 nm | ~225 nm | 5.406 | 3.892 | Major component is Adenine |
| Peak IVa | ~245 nm | ~225 nm | 1.016 | 1.285 | Major component is Guanine |

The fractions are then concentrated and analyzed by SDS-PAGE (see the following) on a 16% gel. Silver staining of the gel demonstrates that only fraction I shows essentially two major silverstainable bands having apparent molecular weights of 4.3 KDa, 5.2 KDa and a minor 7.6 KDa band as shown in FIG. 4.

The relative mass (Mr.):

FIG. 5 shows the relative mass (measurement of molecular weight) of the two major peptide components of Product R resolved on a 16% SDS-Polyacrylamide gel electrophoresis (SDS-PAGE) and stained by silver stain using 'SilverXpress'staining kit from NOVEX, following manufacturer-suggested protocol. Product R is resolved into two major silverstainable bands having apparent molecular weight of about 4.3 and about 5.2 KDa. A minor silverstainable component having molecular weight of about 7.6 KDa is also visible on an overloaded SDS-PAGE gel, and there may be trace amounts of other silverstainable peptides having molecular weights ranging from about 5 KDa to about 14 KDa. Coomassie Blue, a universal protein stain, stains the 4.3 KDa band extremely poorly. The three bands, 4.3 KDa, 5.2 KDa and 7.6 KDa, constitute more than about 90% of the peptides. Thus, Product R consists essentially of molecules having molecular weights below 8 KDa.

TABLE II shows the amino acid compositions of the 5.2 KDa and the 4.3 KDa components. Amino acid analysis of the 5.2 KDa band (sample A) and the 4.3 KDa band (sample B) was performed on a PE Bio-system 420 analyzer with automatic hydrolysis using standard pheno-iso-thiocyanite (PTIC) chemistry.

TABLE II

| Amino acid | Sample A (~5.2 kDa) mol. % | Sample B (~4.3 kDa) mol. % |
|---|---|---|
| Aspartic acid | 9.92 | 8.95 |
| Glutamic acid | 19.27 | 17.30 |
| Serine | 1.03 | 1.23 |

TABLE II-continued

| Amino acid | Sample A (~5.2 kDa) mol. % | Sample B (~4.3 kDa) mol. % |
|---|---|---|
| Glycine | 5.74 | 13.87 |
| Histidine | 2.58 | 3.11 |
| Arginine | 0.69 | 0.52 |
| Threonine | 0.73 | 1.78 |
| Alanine | 5.49 | 8.19 |
| Proline | 13.05 | 15.28 |
| Tyrosine | 4.39 | 3.37 |
| Valine | 9.95 | 5.39 |
| Methionine | 2.92 | 2.21 |
| Isoleucine | 5.47 | 3.45 |
| Leucine | 10.99 | 4.37 |
| Phenylalanine | 3.27 | 1.45 |
| Lysine | 5.12 | 9.53 |

The biochemical properties of the peptides:

Some biochemical properties of the silverstainable peptide components of Product R are analyzed using various catabolic enzymes, as described below:

The treatment with proteinase K (ICN Biochemicals):

Proteinase K is a non-specific broad spectrum protease that cleaves peptide bonds at the C-terminal of aliphatic, aromatic and hydrophobic amino acids. It may cleave all serum peptides completely at 50 μg/ml within one hour. A Product R sample is incubated in a reaction buffer having 10 mM Tris-HCl, pH 7.6; 0.5% of SDS; 1 mM $CaCl_2$; 100 μg/ml of proteinase K at 40° C. for 30 minutes and then subject to SDS-PAGE on a 16% gel as described above. Under such condition, the silver stain of Product R does not show significant change. However, when the amount of proteinase K is increased to 800 μg/ml and the incubation time is extended to one hour, the 5.2 KDa band disappears but there is no obvious change of the 4.3 KDa band.

The treatment with trypsin (Boehringer Mannheim, USA):

Trypsin is a serine protease, which specifically cleaves peptide bonds of lysine and arginine at the C-terminal at pH 7.5–9.0. A Product R sample is incubated in a reaction buffer having 100 mM Tris-HCl, pH 8.0, 0.1% SDS and 250 μg/ml of sequencing grade trypsin at 25° C. for 19 and then subject to SDS-PAGE on a 16% gel. While serum proteins will be broken down to peptides smaller than 4.3 KDa under such reaction conditions, none of the silverstainable components of Product R are affected by trypsin.

The treatment with chymotrypsin (Boehringer Mannheim, USA):

Chymotrypsin is a serine protease that specifcally hydrolyses the peptide bonds of tyrosine, phenylalanine and tryptophan at C-terminals. It also cleaves peptide bonds of leucine, methionin, alanine, aspartic acid and glutamicacid at C-terminals at relatively lower rates. A Product R sample is incubated in a reaction buffer containing 100 mM Tris-HCl, pH 7.6, 10 mM $CaCl_2$ and 250 μg/ml of sequencing grade chymotrypsin at 25° C. for 19 hours and then subject to SDS-PAGE on a 16% gel. Chymotrypsin treatment significantly reduces the intensity of the 5.2 KDa and the 7.6 KDa bands but have no apparent effect on the 4.3 KDa band.

The treatment with pronase (Boehringer Mannheim, USA):

Pronase is a non-specific protease, acts on both native and denatured proteins. It breaks down virtually all proteins into their individual amino acids. The preparation contains various types of endo-peptidases such as srine and metalloproteases, exo-peptidases such as carboypepsidases, neutral protease and neutral and alkaline phosphatases. A Product R sample is incubated in a reaction buffer containing 100 mM Tris-HCl, pH 7.4; 10 mM $CaCl_2$; 0.1% SDS and 2 mg/ml of pronase from S. griseus at 40 ° C. for 75 minutes and then subject to SDS-PAGE on a 16% gel. All silver-stainable components disappear after such treatment of pronase.

The treatment with N-glycosidase F (Boehringer Mannheim, USA):

N-glycosidase F cleaves all types of asparagine bound N-glycans provided that the amino group and the carboxyl group are present in a peptide linkage and the oligosaccharide has the minimum length of the chitobiose core unit. A Product R sample is incubated in a reaction buffer containing 0.4X Dulbecco's PBS (where 1X PBS contains 1.47 mM $KH_2PO_4$, 2.67 mM KCl, 138 mM NaCl and 8.1 mM $Na_2PO_4$ $7H_2O$), 0.1% SDS, 0.5% NP40 and 50 units/ml of recombinant N-glycosidase F at 37° C. for 4 hours and subject to SDS-PAGE on a 16% gel. The treatment N-glycosidase F does not alter the intensity of any of Product R bands on the 16% SDS gel. The resistance to N-glycosidase F indicates the lack of asparagine bound N-glycan, which is commonly observed in glycoproteins.

The treatment with ribonuclease A (ICN Biochemicals, USA)

Ribonuclease A is a pryimidine specific endoribonuclease that acts on single stranded RNA. A Product R sample is incubated in a reaction buffer containing 10 mM Tris-HCl, pH 7.4, 3 mM $MgCl_2$, and I mg/ml of bovine pancreatic Ribonuclease A at 37° C. for about 1 hour and subject to SDS-Page on a 16% gel. Ribonuclease A does not alter the intensity of any of the Product R bands resolved by 16% SDS-PAGE gel. The resistance to ribonuclease A excludes the possibility of the presence of a RNA fragment attached to the peptide.

The treatment with alkaline phosphatase (Life Technologies, USA):

Calf thymus alkaline phosphatase (CIAP) is a phosphomonoesterase that hydrolyses 5'-phosphate groups from DNA, RNA and nucleotides. A Product R sample is incubated in a reaction buffer provided by the manufacturer of the enzyme and 200 units/ml CIAP at 37° C. for about one hour and subjected to SDS-PAGE on a 16% gel. CIAP does not alter the intensity of any of the Product R bands resolved by SDS-PAGE.

A summary of the above described treatments by catabolic enzymes is provided in the following TABLE III, and the results of the treatment are shown in FIG. 5, wherein "–" represents no substantial alteration of the stainable bands and "+" represents substantial alteration of the stainable bands.

TABLE III

| | Sensitivity of the Peptide Components of Product R (SDS-PAGE) | | |
|---|---|---|---|
| Enzyme | 4.3 KDa | 5.2 KDa | 7.6 KDa |
| Proteinase K (100 μg/ml) | – | +/– | ?* |
| (800 μg/ml) | – | + | ?* |
| Trypsin (250 μg/ml) | – | – | – |
| Chymotrypsin (250 μg/ml) | – | + | + |
| Pronase (2 mg/ml) | + | + | + |
| N-glycosidase F (50 units/ml) | – | – | – |
| Ribonuclease A (1 mg/ml) | – | – | – |
| Alkaline Phosphatase (200 units/ml) | – | – | – |

* This band is not clearly identified because of the presence of the enzyme fragments in that region.

The complexity of these enzymatic digestion patterns suggest that the peptide components of Product R may be conjugated with other molecules such a mono-nucleotides and/or carbohydrates, or intra/inter molecularly rosslinked.

RNA gel electrophoresis:

Neither agarose nor polyacrylamaide gel electrophoresis for nucleic acids generates any ethidium bromide stainable bands, indicating that there are no RNA fragments in Product R.

The effect of Product R on the phagocytosis:

FIGS. 7 and 8 are flow cytomeric histograms representing the cell-associated fluorescence, showing the effect of Product R on phagocytosis of Dextran-FITC or Dextran-BoDipyFL after 24 hours and 8 days of the Product R treatment, respectively. The effects of Product R on phagocytosis is tested using a human monocytic cell line, U937. The U937 cells are cultured in a medium having 5% of Product R, or 5% of PBS as a control, for 24 hours prior to the Dextran-FITC test, or 8 days prior to Dextran-BoBipyFl test. To measure phagocytosis, the cells are continuously fed with a phagocytic marker such as fluorescently-labeled Dextran-FITC for 5, 15, 30 and 45 minutes as indicated in FIG. 5, or Dextran-BoDipyFL for 5, 15, 25 and 40 minutes as indicated in FIG. 6 at 37° C. The quantity of a cell-associated fluorescence following phagocytic uptake is monitored using flow cytometry analysis according essentially to the method described by Sallusto, F. et al. (1995), J. Exp. Med., 182:389–400, which is herein incorporated by reference in its entirety. In these tests, the background values have been subtracted from those of the experimental samples and dead cells have been excluded from the data using propidium iodide exclusion.

Each of FIGS. 7 and 8 shows an overlay of the log fluorescence versus cell number for the PBS control (purple), the Product R treatment (green) and the background Dextran binding to cells (black). The purple curves (PBS control) are substantially overlapped with the green curves (Product R) at each time point, indicating that Product R does not inhibit phagocytosis of human monocytic cells.

Other biological functions of Product R:

Some of other known biological functions of Product R have been described in U.S. Pat. Nos. 5,807,840, 5,807,839 and 5,902,786; U.S. patent application Ser. Nos. 08/838,077, 08/838,069, 08/835,793, 08/835,794, 08/833,950, 08/837,992, 08/837,988, 08/838,070, 08/834,190, 08/835,791, 08/838,134, 08/839,651, 08/835,796, 08/964,250, 08/964,427, 08/923,516, 08/923,343, 08/922,888, 09/189,172, 09/007,565, 09/316,624, 09/316,374, 09/257,739 and the publication by Hirschman et al., J. Investig. Med. (1996; 44:347–351. These patents, patent applications and publication are herein incorporated by references in their entireties.

Conclusions

It is thus determined that the composition of Product R prepared according to the present described methods comprises nucleotides and peptides having molecular weights not more than 14 KDa, primarily not more than 8 KDa. The peptide components of Product R are unevenly distributed and typically located at two major silverstainable bands having molecular weights of 4.3 KDa, 5.2 KDa and a minor band of 7.6 KDa.

The UV absorption spectrum of Product R typically shows a maximum absorption at 260 nm and a trough at 235 nm, and the characteristic ratios of the absorbance of 260 nm over absorbance at 280 nm is 1.998 and at 260 nm over 230 nm is 1.359.

The HPLC profile of Product R comprises fractions of A, B, C, D, E, F, G, H, I, J, K, L and M as shown in FIG. 2.

The BioGel P-2 Gel filtration profile of Product R comprises fractions of I, Ia, II, IIa, IIb, III, IIIa, IV and IVa as shown in FIG. 3.

Comparison Between The Conventional Composition of Reticulose® And Product R

The composition of Product R as made according to the teachings of the present invention is compared with the conventional composition of RETICULOSE® with respect to their molecular weights (MW) and ultraviolet (UV) absorbancies (A) at wavelength of 230 nm, 260 nm and 280 nm, as shown in TABLE IV. While the components having molecular weights below 15 KDa of RETICULOSE® have been reported to inhibit the phagocytosis, the present application demonstrates that Product R does not inhibit the phagocytosis.

TABLE IV

| | MW | UV | | I/PH* |
| --- | --- | --- | --- | --- |
| | | $A_{260/280}$ | $A_{260/230}$ | |
| Product R | <14 KDa | 1.998 | 1.359 | No |
| RETICULOSE ® | 1–25 KDa | 2.839 | 1.198 | Yes |

*inhibition of phagocytosis by molecules having molecular weight below 15 KDa

Thus, Product R differs substantially from RETICULOSE® in their composition and bilogical functions.

TABLE V is a comparison between the relative amounts of the starting materials used for the preparations of the present therapeutic composition Product R and the conventional composition RETICULOSE®.

TABLE V

| STARTING MATERIALS FOR INITIAL REACTION IN TEN LITERS | RETICULOSE ® | Product R |
| --- | --- | --- |
| casein | 250 grams | 140 grams |
| beef peptone | 150 grams | 68.4 grams |
| serum albumin | 15 grams | 13 grams |
| RNA | 80 grams | 88 grams |
| NaOH | 75 grams | 66 grams |

About 221 grams proteins are used in the initial reaction for the preparation of Product R, while about 415 grams for the preparation of RETICULOSE®. Thus, the initial protein concentration for the RETICULOSE® preparation is twice as much as that for the Product R preparation.

The following example only serves as an illustration of the process of making Product R and should not be construed as a limitation of the present invention.

EXAMPLE

Suspend about 35.0 g of casein, about 17.1 g of beef peptone, about 22.0 g of nucleic acid (yeast RNA), about 3.25 g bovine serum albumin in about 2.5 liters of water for injection USP at about 3 to 7° C. in a suitable container and gently stir until all the ingredients have been properly wet. Carefully add while stirring about 16.5 g of sodium hydroxide (reagent grade ACS) and continue stirring until sodium hydroxide completely dissolved. Autoclave at about 9 lbs. pressure and 200°–230° F. for a period of time until RNA is completely digested, for example, about 4 hours. At the end of the period, the autoclave is stopped and the reaction flask and contents are permitted to slowly cool to ambient temperature. Then cool for at least six hours at about 3°–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/100 ml, the final volume is approximately 5 liters. The pH is then adjusted with either concentrated HCl (reagent grade ACS) or 1.0 normal NaOH to about 7.3–7.6 range. The diluted solution is then filtered again through 0.2 micron filters with inert gas at low pressure. The final filtrate is then filled and sealed into 2 ml glass ampules while in an inert gas atmosphere. The amplules are collected and autoclaved for final sterilization at 240° F. and 14–16 pounds pressure for about 30 minutes. Following the sterilization cycle, the ampules with Product R are cooled and washed.

All quantities are subject to plus or minus 15% variation of pH, volume, and analytical adjustments.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A peptide nucleic acid composition that absorbs light at wavelengths 230 nm, 260 nm and 280 nm so as to result in 260 nm/280 nm absorption ratio of about 1.998 and 260 nm/230 nm absorption ratio of about 1.359, comprising molecules of nucleotides resulting from a plant RNA and pleptides resulting from a mixture of casein, beef peptone and bovine serum albumin, said molecules having non-uniformly distributed molecular weights.

2. The composition of claim 1, wherein said nucleotides are mono-nucleotides.

3. The composition of claim 1, wherein said molecules have non-uniformly distributed molecular weights in a range from zero to substantially not more than 14 KDa.

4. The composition of claim 1, wherein said molecules have non-uniformly distributed molecular weights in a range from zero to substantially not more than 8 KDa.

5. The composition of claim 1, wherein said molecules have substantial concentrations at molecular weights of substantially 5.2 KDa and 4.3 KDa.

6. A method for preparing a peptide nucleic acid composition that absorbs light at wavelengths 230 nm, 260 nm and 280 nm so as to result in 260 nm/280 nm absorption ratio of about 1.998 and 260 nm/230 nm absorption ratio of about 1,359, said composition containing molecules of nucleotides and peptides having non-uniformly distributed molecular weights, comprising the steps of:

a. forming a mixture including a protein combination consisting oc casein, beef peptone and bovine serum albumin, a plant RNA and a base in water, wherein the ratio of said protein combination to said water is in a range from about 1.5/100 to about 2.5/100 by weight;

b. processing said mixture at an elevated temperature and an elevated pressure so as to form a solution and insoluble elements;

c. removing said insoluble elements;

d. diluting said solution with water; and e. after performing steps b, c and d, adjusting the pH of said solution to a physiologically acceptable pH.

7. The method of claim 6, wherein the ratio of said protein combination of said water is about 2.2/100 by weight.

8. The method of claim 6, wherein said nucleotides are mono-nucleotides.

9. The method of claim 6, wherein said molecules have non-uniformly distributed molecular weights in a range from zero to substantially not more than 14 KDa.

10. The method of claim 6, wherein said molecules have non-uniformly distributed molecular weights in a range from zero to substantially not more than 8 KDa.

11. The method of claim 6, wherein said molecules have substantial concentrations at molecular weights of substantially 5.2 KDa and 4.3 KDa.

* * * * *

UNITED STATES PATENT AND TRADEMARK OFFICE
CERTIFICATE OF CORRECTION

PATENT NO. : 6,303,153 B1
DATED : October 16, 2001
INVENTOR(S) : Bernard Friedland et al.

It is certified that error appears in the above-identified patent and that said Letters Patent is hereby corrected as shown below:

Column 1,
Line 7, delete "pending".
Line 10, "their" should be -- its --.
Line 25, delete "was.".
Line 54, "equals" should be -- equal --.

Column 2,
Line 3, "methods" should be -- method --.

Column 3,
Line 5, "form" should be -- from --.
Line 10, delete "of" after "16%".
Lines 19 and 21, "histograms" should be -- histogram --.

Column 4,
Line 29, insert -- of -- after "regardless.".
Line 62, "uM" should be -- µM --.
Line 65, "A" should be -- Å --.

Column 5,
Line 37, "absorbences" should be -- absorbance --.

Column 7,
Line 51, "methionin" should be -- methionine --.
Line 51, "glutamicacid" should be -- glutamic acid --.
Line 58, "have" should be -- has --.
Line 63, "srine" should be -- serine --.

Column 8,
Line 21, insert -- : -- after "USA)".
Line 22, "pryimidine" should be -- pyrimidine --.
Line 25, "I" should be -- 1 --.
Line 66, "such a" should be -- such as --.
Line 67, "rosslinked" should be -- crosslinked --.

Column 9,
Line 44, "(1996" should be -- (1996) --.
Line 50, "present" should be -- presently --.

UNITED STATES PATENT AND TRADEMARK OFFICE
CERTIFICATE OF CORRECTION

PATENT NO. : 6,303,153 B1
DATED : October 16, 2001
INVENTOR(S) : Bernard Friedland et al.

It is certified that error appears in the above-identified patent and that said Letters Patent is hereby corrected as shown below:

<u>Column 10,</u>
Line 25, "bilogical" should be -- biological --.
Line 59, insert -- is -- after "hydroxide.".

<u>Column 11,</u>
Line 12, "amplules" should be -- ampules --.
Line 42, "pleptides" should be -- peptides --.

<u>Column 12,</u>
Line 19, "oc" should be -- of --.

Signed and Sealed this

Eighteenth Day of April, 2006

JON W. DUDAS
*Director of the United States Patent and Trademark Office*